(12) United States Patent
Ezoe et al.

(10) Patent No.: US 7,964,414 B2
(45) Date of Patent: Jun. 21, 2011

(54) BIOSENSOR WITH SUPPRESSED NON-SPECIFIC ADSORPTION

(75) Inventors: Toshihide Ezoe, Kanagawa (JP); Taisei Nishimi, Kanagawa (JP); Yukou Saito, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 810 days.

(21) Appl. No.: 11/377,554

(22) Filed: Mar. 17, 2006

(65) Prior Publication Data

US 2006/0246512 A1 Nov. 2, 2006

(30) Foreign Application Priority Data

Mar. 22, 2005 (JP) ................................. 2005-082270

(51) Int. Cl.
*G01N 33/543* (2006.01)
*C12M 1/34* (2006.01)

(52) U.S. Cl. ..................... 436/518; 422/82.11; 427/2.11; 427/2.13; 427/163.2; 427/337; 427/402; 427/404; 435/7.1; 435/287.1; 436/524; 436/525; 436/805

(58) Field of Classification Search ............... 435/287.1, 435/287.9, 970; 436/524, 525, 528, 807
See application file for complete search history.

(56) References Cited

U.S. PATENT DOCUMENTS

| | | | |
|---|---|---|---|
| 5,240,994 A * | 8/1993 | Brink et al. .................. 525/54.2 |
| 5,242,828 A | 9/1993 | Bergström et al. |
| 5,645,717 A * | 7/1997 | Hjerten et al. ............. 210/198.2 |
| 5,763,191 A | 6/1998 | Knoll et al. |
| 6,090,545 A * | 7/2000 | Wohlstadter et al. ............. 435/6 |
| 6,489,102 B2 * | 12/2002 | Corn et al. ........................ 435/6 |
| 6,597,456 B2 | 7/2003 | Kubo et al. |
| 6,730,772 B2 * | 5/2004 | Shastri .......................... 528/354 |
| 7,214,500 B2 | 5/2007 | Kataoka et al. |
| 2005/0142028 A1 | 6/2005 | Kataoka et al. |

FOREIGN PATENT DOCUMENTS

| | | |
|---|---|---|
| CA | 2 262 011 A1 | 8/1999 |
| JP | 11-337552 JP | 12/1999 |
| JP | 11-352127 | 12/1999 |
| JP | 2004-125462 | 4/2004 |
| WO | WO 01/86301 A1 | 11/2001 |
| WO | 03/076933 A1 | 9/2003 |

OTHER PUBLICATIONS

Pavey et al. SPR analysis of the total reduction of protein adsorption to surfaces coated with mixtures of long-and short-chain polyethylene oxide block copolymers. Biomaterials (1999) 20(9):885-890.*
Fluke Laboratory Chemicals and Analytical reagents, 1999/2000, p. 91.*

* cited by examiner

*Primary Examiner* — Mark L Shibuya
*Assistant Examiner* — Galina Yakovleva
(74) *Attorney, Agent, or Firm* — Sughrue Mion, PLLC

(57) ABSTRACT

The present invention provides a biosensor, wherein non-specific adsorption on a surface that does not retain a physiologically active substance (reference unit) is suppressed. The biosensor of the invention includes a substrate having at least two types of surfaces on a single plane, wherein at least one of the surfaces does not retain a physiologically active substance, and wherein at least two types of hydrophilic compounds with different molecular weights are bound to the surface that does not retain a physiologically active substance.

11 Claims, 1 Drawing Sheet

BIOSENSOR WITH SUPPRESSED NON-SPECIFIC ADSORPTION

TECHNICAL FIELD

The present invention relates to a biosensor and a method for analyzing an interaction between biomolecules using the biosensor. Particularly, the present invention relates to a biosensor which is used for a surface plasmon resonance biosensor and a method for analyzing an interaction between biomolecules using the biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open (Kokai) No. 9-264843).

On the other hand, in order to eliminate influence of measurement disturbance (changes in temperature, concentration, and pressure) thereby reducing baseline fluctuation, a measurement unit for measuring a specific binding reaction between a physiologically active substance and a test substance, and a reference unit wherein such a binding reaction is not carried out, preferably exist on a single plane of the above-described biosensor, and are located as close as possible to each other. Thus, it became necessary to allow a reference unit and a measurement unit to coexist on an SPR sensor surface using a thin polymer film.

For example, Japanese Patent Laid-Open (Kokai) No. 2004-125462 describes a biochip for immobilizing biomolecules or an aggregate of such biomolecules on the surface, which is characterized in that a substance acting as an origin of immobilization or a substance having a functional group is immobilized on a portion for immobilizing the above biomolecules or aggregate of biomolecules (immobilization portion), and in that a hydrophilic compound is immobilized on a background portion other than the immobilization portion. However, in the case of the biochip described in Japanese Patent Application Laid-Open (Kokai) No. 2004-125462, when a crude sample (for example, a cell extract) is flown over it as an analyte, non-specific adsorption takes place, and a specific binding signal cannot be obtained. Thus, this biochip has been problematic in that it is not resistant particularly to the non-specific adsorption of small molecules.

DISCLOSURE OF INVENTION

It is an object of the present invention to solve the aforementioned problem. That is to say, it is an object of the present invention to provide a biosensor, wherein non-specific adsorption on a surface that does not retain a physiologically active substance (reference unit) is suppressed.

As a result of intensive studies directed towards achieving the aforementioned object, the present inventors have found that in a biosensor comprising a substrate having at least two types of surfaces on a single plane, non-specific adsorption on the surface that does not have a physiologically active substance (reference unit) can be suppressed by allowing at least two types of hydrophilic compounds with different molecular weights to be bound to the surface that does not retain a physiologically active substance, thereby completing the present invention.

Thus, the present invention provides a biosensor which comprises a substrate having at least two types of surfaces on a single plane, wherein at least one of said surfaces does not retain a physiologically active substance, and wherein at least two types of hydrophilic compounds with different molecular weights are bound to said surface that does not retain a physiologically active substance.

Preferably, the biosensor of the present invention is obtained by allowing at least two types of hydrophilic compounds with different molecular weights to bind to the surface that does not retain a physiologically active substance in decreasing order of the molecular weight of each type of compound.

Preferably, the average molecular weight of a hydrophilic compound with the smallest molecular weight is between 100 and 1,000.

Preferably, the average molecular weight of a hydrophilic compound with the largest molecular weight is between 1,000 and 1,000,000.

Preferably, at least two types of hydrophilic compounds, the difference between the average molecular weights of which is at least 500, are bound to the surface that does not retain a physiologically active substance.

Preferably, the hydrophilic compounds are selected from among gelatin, alginic acid, chitosan, dextran, polyvinyl alcohol, polyethylene glycol or a derivative thereof, carragheenan, agarose, polyacrylic acid, and polyacrylamide.

Preferably, the substrate is composed of a metal surface or metal film.

Preferably, the metal surface or metal film consists of a free electron metal selected from the group consisting of gold, silver, copper, platinum, and aluminum.

Preferably, the biosensor of the present invention is used in non-electrochemical detection, and is more preferably used in surface plasmon resonance analysis.

Another aspect of the present invention provides a method for immobilizing a physiologically active substance on the surface of a biosensor, which comprises a step of allowing the biosensor of the present invention as mentioned above to come into contact with a physiologically active substance, so as to prepare a surface to which said physiologically active substance has been bound, and a surface to which said physiologically active substance has not been bound, on said biosensor surface.

Further another aspect of the present invention provides a method for detecting or measuring a substance interacting with a physiologically active substance, which comprises a step of allowing a test substance to come into contact with the biosensor of the present invention as mentioned above.

Preferably, the substance interacting with the physiologically active substance is detected or measured by a non-electrochemical method, and more preferably the substance interacting with the physiologically active substance is detected or measured by surface plasmon resonance analysis.

BEST MODE FOR CARRYING OUT THE INVENTION

Figure 1:
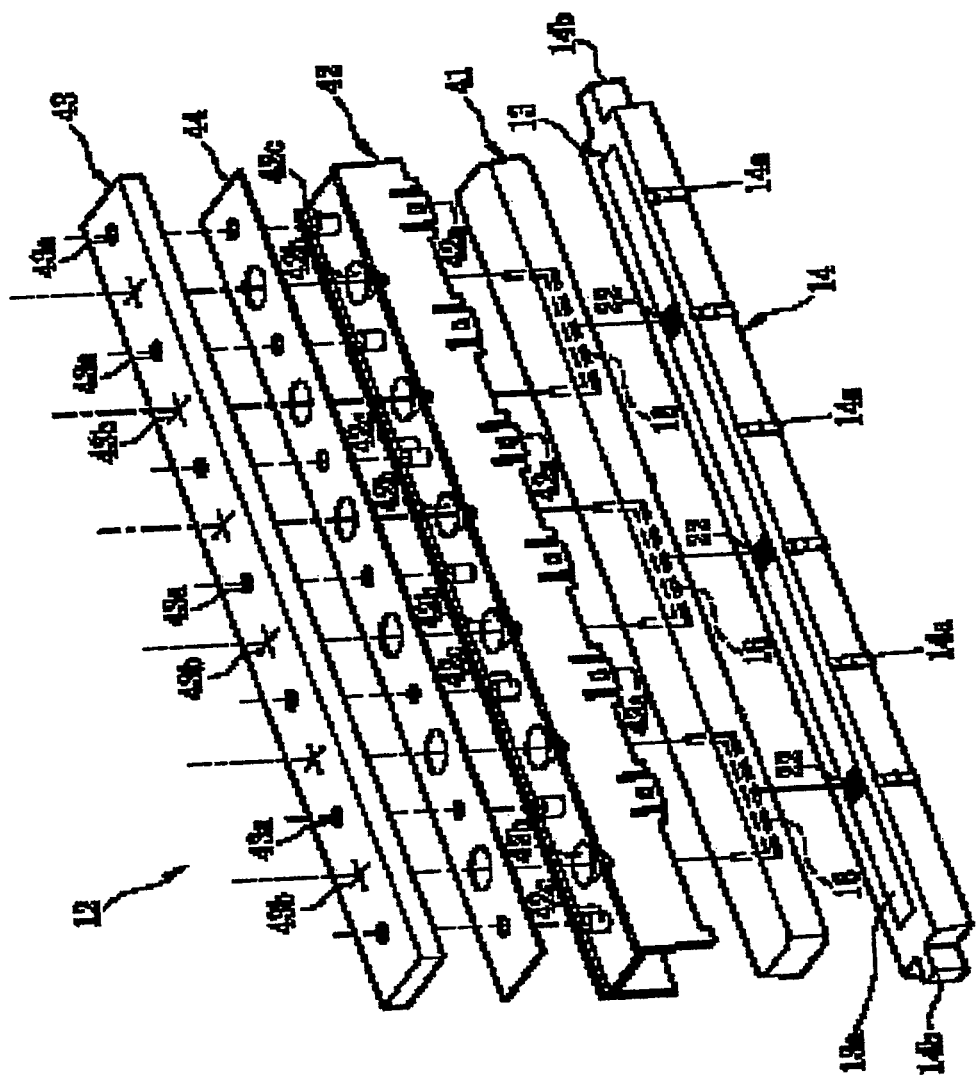
FIG. 1 shows a plastic prism used in the examples.

The embodiments of the present invention will be described below.

The biosensor of the present invention has a biomolecule immobilization unit (measurement unit) and a biomolecule non-immobilization unit (reference unit), and it is characterized in that two or more types of hydrophilic compounds with different molecular weights are bound to the biomolecule non-immobilization unit (reference unit). Preferably, such two or more types of hydrophilic compounds with different molecular weights are allowed to successively bind to the biomolecule non-immobilization unit in decreasing order of the molecular weight of each type of compound.

In the biosensor of the present invention, a substrate is coated with a hydrophilic compound. Examples of such a hydrophilic compound used in the present invention may include gelatin, alginic acid, chitosan, dextran, polyvinyl alcohol, polyethylene glycol or a derivative thereof, carragheenan, agarose, polyacrylic acid, and polyacrylamide. These may also be biocompatible porous matrixes, such as a so-called hydrogel. The thickness of such a hydrophilic compound is between several nm and several hundreds of nm, and preferably between 10 and 500 nm. An example of the hydrophilic compound used in the present invention is a hydrogel described in Merrill et al. (1986), Hydrogels in Medicine and Pharmacy, vol. III, Chapter 1, CRC, edited by Peppas N A. As such a hydrophilic compound, polyethylene glycol is particularly preferably used.

The aforementioned hydrophilic compound may be immobilized on a substrate via a self-assembling film or a hydrophobic polymer compound, as described in the present specification below. Or, it may also be directly formed on a substrate from a solution containing a monomer. Further, it is also possible that the aforementioned hydrophilic compound be crosslinked. Such crosslinking of a hydrophilic compound is obvious to persons skilled in the art.

In the present invention, the average molecular weight of a hydrophilic compound with the smallest molecular weight is preferably between 100 and 1,000, and the average molecular weight of a hydrophilic compound with the largest molecular weight is preferably between 1,000 and 1,000,000. In addition, it is preferable that at least two types of hydrophilic compounds, wherein the difference between their average molecular weights is at least 500 (more preferably, 1,000 or greater), be allowed to bind to the surface that does not retain a physiologically active substance.

In the present invention, the term "surface that does not retain a physiologically active substance" is used to mean a surface, wherein the amount of a physiologically active substance retained thereon is less than one tenth the amount of the above substance retained on a surface for retaining such a physiologically active substance, when the surface has been treated to immobilize the physiologically active substance thereon (for example, the surface is treated with a mixture of carboxylic acid activators, EDC and NHS, and then treated with a physiologically active substance).

The surface for retaining a physiologically active substance is preferably a surface which has a functional group for binding the physiologically active substance. The surface that does not retain such a physiologically active substance is preferably a surface which does not have a functional group for binding the physiologically active substance.

Specific examples of a functional group for binding a physiologically active substance may include —COOH, —NR$^1$R$^2$ (wherein each of R$^1$ and R$^2$ independently represents a hydrogen atom or a lower alkyl group), —OH, —SH, —CHO, —NR$^3$NR$^1$R$^2$ (wherein each of R$^1$, R$^2$, and R$^3$ independently represents a hydrogen atom or a lower alkyl group), —NCO, —NCS, an epoxy group, and a vinyl group. Herein, the number of carbon atoms contained in a lower alkyl group is not particularly limited, but it is generally approximately C1 to C10, and preferably C1 to C6.

Preferred examples of such a functional group for binding a physiologically active substance may include a carboxyl group, an amino group, and a hydroxyl group.

A functional group for binding a physiologically active substance is selected depending on a method for immobilizing the physiologically active substance in the present invention. That is to say, a certain type of functional group (for example, a hydroxyl group, etc.) may be considered to be a "functional group for binding a physiologically active substance," or may not considered to be such a functional group, depending on a method for immobilizing the physiologically active substance.

When the functional group for binding a physiologically active substance is a carboxyl group, for example, a method of generating an active ester by the combined use of carbodiimide with N-hydroxysuccinimide, so as to generate a covalent bond with an amino group of the physiologically active substance, is often used. In this case, a functional group incapable of binding a physiologically active substance, such as a hydroxyl group, an amino group, or polyethers, has been introduced into a surface which has no functional groups for binding such a physiologically active substance.

Moreover, when the functional group for binding a physiologically active substance is an amino group, a method of allowing glutaraldehyde to act thereon and then generating a covalent bond with an amino group of the physiologically active substance, and a method of oxidizing the physiologically active substance with periodate and then allowing the above substance to directly covalently bind to the amino group, are often used. In such cases, it may be possible that a functional group incapable of binding a physiologically active substance, such as a hydroxyl group, a carboxyl group, or polyethers, have been introduced into a surface which has no functional groups for binding such a physiologically active substance.

Furthermore, when the functional group for binding a physiologically active substance is a hydroxyl group, a method of allowing a polyepoxy compound or epichlorohydrin to act thereon and then generating a covalent bond with an amino group of the physiologically active substance is often used. As a chemical reaction, a direct ether bond formation reaction using halogenated alkyl is also applied. However, when such a reaction is applied to a physiologically active substance, there are cases where it becomes difficult to maintain the physiological activity. In such a case, it may be possible that a functional group incapable of binding a physiologically active substance, such as a water-soluble group (for example, a polyether of polyethylene glycol), which has no hydrogen with reactivity (specifically, hydrogen of a hydroxyl group, an amino group, or a carboxyl group), have been introduced into a surface which has no functional groups for binding such a physiologically active substance.

When a surface for retaining a physiologically active substance and a surface that does not retain a physiologically active substance are formed on a single plane of a substrate, it is preferable that a solid (for example, a stamp) be not allowed to come into contact with a detection region. Specific means may include a means for preparing a droplet on the tip of a syringe, so as to allow only such a droplet to come into contact with a detection region, a means for spraying such droplets from a nozzle, a means for preparing a flow channel and flowing a reaction solution over it, and a means for establishing a diaphragm and filling it with a liquid. Of these, a means for using a diaphragm is preferable.

When the interaction between a physiologically active substance immobilized on the biosensor of the present invention and a test substance is measured, a surface for retaining a physiologically active substance in the biosensor is used as a measurement unit, whereas a surface that does not retain such a physiologically active substance is used as a reference unit. Further, using several different substances as physiologically active substances to be bound, it may also be possible to establish multiple measurement units.

In the present invention, a self-assembling film is formed on a substrate, or a substrate is coated with a hydrophobic polymer, and then the surface thereof can be coated with a hydrophilic compound. Hereafter, the self-assembling film and a hydrophobic polymer compound will be described.

The term "self-assembling film" is used in the present invention to mean an ultra-thin film, such as a monomolecular film or an LB film, which has tissues with certain order formed by the mechanism of a film material itself in a state where no detailed controls are given from the outside. By such self-assembling, a structure or pattern with certain order can be formed over a long distance in a nonequilibrium situation.

For example, such a self-assembling film can be formed from a sulfur-containing compound. Formation of a self-assembling film from a sulfur-containing compound on a gold surface is described, for example, in Nuzzo R G et al. (1983), J. Am. Chem. Soc., vol. 105, pp. 4481-4483, Porter M D et al. (1987), J. Am. Chem. Soc., vol. 109, pp. 3559-3568, Troughton E B et al. (1988), Langmuir, vol. 4, pp. 365-385.

Such a sulfur-containing compound is preferably represented by X—R—Y.

X is a group having binding ability to a metal film. Specific examples of X, which is preferably used herein, may include asymmetric or symmetric sulfide (—SSR'Y", —SSRY), sulfide (—SR'Y", —SRY), diselenide (—SeSeR'Y", —SeSeRY), selenide (SeR'Y", —SeRY), thiol (—SH), nitrile (—CN), isonitrile, nitro (—$NO_2$), selenol (—SeH), a trivalent phosphorus compound, isothiocyanate, xanthate, thiocarbamate, phosphine, thio acid, and dithio acid (—COSH, —CSSH).

R (and R') are blocked by heteroatoms in some cases. For suitably tight packing, R (and R') are preferably linear (not branched) chains, and in some cases, are hydrocarbon chains containing double and/or triple bonds. The length of such a chain is generally 5 or more atoms, preferably 10 or more atoms, and more preferably 10 to 30 atoms. A carbon chain can be perfluoridated in some cases. When it is an asymmetric molecule, R' or R may also be H.

Y and Y" are groups for binding a hydrophilic compound. Y and Y" are preferably identical to each other, and they have properties such that they are able to bind to a hydrophilic compound (for example, a hydrogel, etc.), directly or after activation. Specific examples of Y and Y" that can be used herein may include a hydroxyl group, a carboxyl group, an amino group, an aldehyde group, a hydrazide group, group, a carbonyl group, an epoxy group, and a vinyl group.

The compound represented by X—R—Y, which is in the form of a tightly packed monolayer, is able to attach to the surface of a metal, by the binding of the group represented by X to the metal.

Specific examples of the compound represented by X—R—Y may include 10-carboxy-1-decanethiol, 4,4'-dithiodibutylic acid, 11-hydroxy-1-undecanethiol, 11-amino-1-undecanethiol, and 16-hydroxy-1-hexadecathiol.

A hydrophobic polymer used in the present invention is a polymer having no water-absorbing properties. Its solubility in water (25° C.) is 10% or less, more preferably 1% or less, and most preferably 0.1% or less.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A substrate is coated with a hydrophobic polymer according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of a hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperature is preferably −20° C. to 100° C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit:$(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value $\delta$ was calculated by the following formula. As the cohesive energy (Ecoh) of each functional group and the mol volume (V), those defined by Fedors were used (R. F. Fedors, Polym. Eng. Sci., 14(2), P147, P472(1974)).

$$\Delta = (\Sigma Ecoh/\Sigma V)^{1/2}$$

Examples of the SP values of the hydrophobic polymers and the solvents are shown below;
Solvent:2-phenoxyethanol:25.3 against polymethylmethacrylate-polystyrene copolymer (1:1):21.0
Solvent:acetonitrile:22.9 against polymethylmethacrylate: 20.3
Solvent:toluene:18.7 against polystyrene:21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably −20° C. to 100° C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent, for the purpose of removing the less volatile solvent.

The coating thickness of a hydrophobic polymer is not particularly limited, but it is preferably between 0.1 nm and 500 nm, and particularly preferably between 1 nm and 300 nm.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

The biosensor of the present invention is obtained by coating a metal surface or metal film with a hydrophilic compound. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, more preferably between 0.5 nm and 500 nm, and particularly preferably between 1 nm and 200 nm. If the thickness exceeds 500 µm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

The biosensor of the present invention preferably has a functional group capable of immobilizing a physiologically active substance on the outermost surface of the substrate. The term "the outermost surface of the substrate" is used to mean "the surface, which is farthest from the substrate," and more specifically, it means "the surface of a hydrophilic polymer compound applied on a substrate, which is farthest from the substrate."

In order to introduce these functional groups into the outermost surface, a method is applied that involves applying a hydrophilic polymer compound containing a precursor of such a functional group on a metal surface or metal film, and then generating the functional group from the precursor located on the outermost surface by chemical treatment.

A physiologically active substance is covalently bound to the above-obtained surface for a biosensor via the above functional group, so that the physiologically active substance can be immobilized on the metal surface or metal film.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme or nucleic acid, an amino group, thiol group or the like of the physiologically active substance is covalently bound to a functional group located on a metal surface, so that the physiologically active substance can be immobilized on the metal surface.

A biosensor to which a physiologically active substance is immobilized as described above can be used to detect and/or measure a substance which interacts with the physiologically active substance.

Thus, the present invention provides a method of detecting and/or measuring a substance interacting with the physiologically active substance immobilized to the biosensor of the present invention, to which a physiologically active substance is immobilized, wherein the biosensor is contacted with a test substance.

As such a test substance, for example, a sample containing the above substance interacting with the physiologically active substance can be used.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

The biosensor according to the present invention can be preferably formed and used in a measurement chip that is used for a surface plasmon resonance measurement device comprising a dielectric block, a metal film formed on one side of the dielectric block, a light source for generating a light beam, an optical system for allowing said light beam to enter said dielectric block so that total reflection conditions can be obtained at the interface between said dielectric block and said metal film and so that various incidence angles can be included, and a light-detecting means for detecting the state of surface plasmon resonance by measuring the intensity of the light beam totally reflected at said interface, wherein said measurement chip is basically composed of said dielectric block and said metal film, wherein said dielectric block is formed as a block including all of an incidence face and an exit face for said light beam and a face on which said metal film is formed, and wherein said metal film is unified with this dielectric block.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta$SP), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta$SP) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta$SP) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle (θSP) is measured periodically when a certain period of time has elapsed.

If the test substance contained in the sample solution is bound to the sensing substance, the refractive index of the sensing substance is changed by this binding over time. Accordingly, the above attenuated total reflection angle (θSP) is measured periodically after the elapse of a certain time, and it is determined whether or not a change has occurred in the above attenuated total reflection angle (θSP), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

The sensor chip of the present invention was produced by the following method.
(1) Formation of Gold Film on Plastic Prism
A thin gold film was formed on the top surface of a plastic prism (FIG. 1) obtained by the injection molding of ZEONEX (manufactured by ZEON Corporation) by the following method.
(1-1) Formation of Gold Film
The prism was attached to the substrate holder of a sputter device. After vacuuming (base pressure: $1 \times 10^{-3}$ Pa or less), Ar gas (1 Pa) was introduced therein. Thereafter, while rotating the substrate holder (20 rpm), RF power (0.5 kW) was applied to the substrate holder for approximately 9 minutes, so as to subject the surface of the prism to a plasma treatment. Subsequently, introduction of Ar gas was terminated, followed by vacuuming. Thereafter, Ar gas was introduced again (0.5 Pa), and while rotating the substrate holder (10 to 40 rpm), DC power (0.2 kW) was applied to a Cr target with a size of 8 inch for approximately 30 seconds, so as to form a thin Cr film with a thickness of 2 nm. Subsequently, introduction of Ar gas was terminated, followed by vacuuming. Thereafter, Ar gas was introduced again (0.5 Pa), and while rotating the substrate holder (20 rpm), DC power (1 kW) was applied to an Au target with a size of 8 inch for approximately 50 seconds, so as to form a thin Au film with a thickness of approximately 50 nm. The obtained sample was called chip A.
(2) Application of Polymer
A thin polymer film was formed on the thin gold film of chip A by the following method.
(2-1) Preparation of Polymer Solution A
1.5 g of polymer (F-1) was dissolved in 100 ml of anhydrous MiBK (methyl isobutyl ketone), and the obtained solution was then filtrated with a microfilter with a pore diameter of 0.45 μm. The water content of the anhydrous MiBK was 20 ppm.

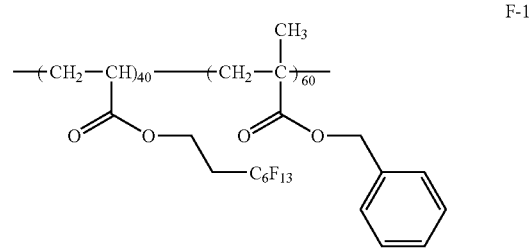

Figure 2:
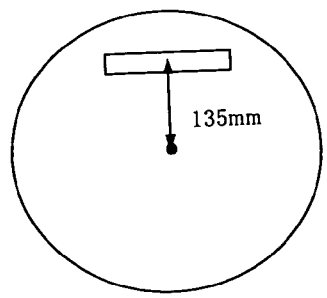
FIG. 2 shows the position of chip A immobilized on a spin-coater.

(2-2) Spin-Coating
Chip A was set to a spin-coater (SC-408S sample hermetically sealed spin-coater; manufactured by Oshikane). Chip A was fixed at the position that was 135 mm from the center of the spin-coater, as shown in FIG. 2. 200 μl of polymer solution A was casted on chip A, such that the entire gold film could be coated with the solution. Thereafter, a windbreak cover was set, such that chip A could be completely coated therewith. Thereafter, the chip was spun at 200 rpm for 60 seconds. After termination of the rotation, the chip was left at rest for 5 minutes.
(2-3) Vacuum Drying
Chip A, which had been spin-coated with the polymer, was subjected to vacuum drying for 16 hours. The obtained sample was called chip B.

(3) Hydrolysis of Polymer Surface

The surface of the thin polymer film of chip B was hydrolyzed by the following method, so as to generate a COOH group on the outermost surface.

(3-1) Hydrolysis

Chip B was immersed in a 1 N NaOH solution, and it was then conserved in a thermostatic bath at 60° C. for 16 hours.

(3-2) Washing

The chip was removed from the 60° C. thermostatic bath, and it was subjected to natural cooling for 15 minutes. Thereafter, the chip was washed with ultrapure water. The obtained sample was called chip C.

(4) Binding of 5-Aminovaleric Acid 5-aminovaleric acid was allowed to covalently bind to the COOH group existing on the surface of chip C by the following method.

(4-1) Preparation of Activator Solution and 5-Aminovaleric Acid Solution 0.1 M NHS solution:1.16 g of NHS(N-hydroxysulfosuccinimide) was dissolved in ultrapure water, so as to prepare 100 mL of the solution.

0.4 M EDC solution:7.7 g of EDC (1-ethyl-3-[3-dimethylaminopropyl]carbodiimidehydrochloride) was dissolved in ultrapure water, so as to prepare 100 mL of the solution.

1 M 5-aminovaleric acid solution:11.7 g of 5-aminovaleric acid was dissolved in 80 mL of ultrapure water, and the pH of the solution was then adjusted to pH 8.5 by addition of 1 N NaOH. Thereafter, ultrapure water was further added thereto, so as to prepare 100 mL of the solution.

(4-2) Activation

Chip C was drained using an air gun. Chip C was set in a wet box (a tight box in which a wet cloth had been placed at the bottom, wherein the humidity was maintained at 90% RH or more in a hermetically sealed state). Thereafter, 200 μl of a mixed solution of 100 μl of the 0.1 M NHS solution and 100 μl of the 0.4 M EDC solution was casted thereon. Thereafter, a PET film with a size of 120 mm×8.5 mm and with a thickness of 175 μm was placed thereon, so as to cover the surface while spreading the solution. During this reaction, the ratio of the surface area of the solution, which was not allowed to come into contact with air, to the surface area of the solution, which was allowed to come into contact with air, was 26. The wet box was hermetically sealed, and it was then left at rest at 25° C. for 60 minutes.

(4-3) Washing

The PET film was removed from the sample taken out of the wet box, and the sample was then washed with ultrapure water. The obtained sample was called chip D.

(4-4) 5-Aminovaleric Acid Reaction

A 5-aminovaleric acid reaction was initiated within 1 hour after completion of the activation reaction. First, chip D was drained using an air gun. Chip D was set in a wet box, and 200 μl of a 1 M 5-aminovaleric acid solution was then casted thereon. Thereafter, a PET film with a size of 120 mm×8.5 mm and with a thickness of 175 μm was placed thereon, so as to cover the surface while spreading the solution. During this reaction, the ratio of the surface area of the solution, which was not allowed to come into contact with air, to the surface area of the solution, which was allowed to come into contact with air, was 24. The wet box was hermetically sealed, and it was then left at rest at 25° C. for 90 minutes.

(4-5) Washing

The PET film was removed from the sample taken out of the wet box, and the sample was then washed with ultrapure water. The obtained sample was called chip E.

(5) Formation of Surface that does not Retain Physiologically Active Substance

A portion that does not retain a physiologically active substance was formed on the surface of chip E by the following method. Specifically, using the COOH group of 5-aminovaleric acid existing on the surface of chip E, the following PEG derivatives were allowed to covalently bind to a specific area of chip E.

(5-1) Preparation of Reaction Solutions

20% PEG derivative solutions:4.5 g of each of the following PEG derivatives was dissolved in 18.5 mL of ultrapure water and 4 mL of 1 N NaOH.

PEG derivative (1):NH2-(CH2CH2O)n-CH2CH2OH, molecular weight of 5,000

PEG derivative (2):NH2-(CH2CH2O)n-CH2CH2OH, molecular weight of 2,000

PEG derivative (3):NH2-(CH2CH2O)4-CH2CH2OH, molecular weight of 237

0.1 M Sulfo-NHS solution:2.04 g of NHS was dissolved in ultrapure water, so as to prepare 100 mL of the solution.

0.4 M EDC solution:7.7 g of EDC was dissolved in ultrapure water, so as to prepare 100 mL of the solution.

(5-2) Activation

Chip E was drained using an air gun, and it was then immobilized on the seating of a dispenser manufactured by Musashi Engineering, Inc. Subsequently, a mixed solution of 2 mL of the 0.1M Sulfo-NHS solution and 2 mL of the 0.4M EDC solution was poured into a syringe. 15 μL each of the above mixed solution was spotted on 6 points of chip E at intervals of 18 mm. The diameter of a droplet was approximately 3.5 mm. After such spotting, chip E was placed in a wet box, and the wet box was then hermetically sealed. It was left at rest at 25° C. for 60 minutes.

(5-3) Washing

The sample removed from the wet box was washed with pure water. The obtained sample was called chip F.

(5-4) Binding of PEG Derivative

Chip F was drained using an air gun, and it was then immobilized on the seating of a dispenser manufactured by Musashi Engineering, Inc. Subsequently, each of the PEG derivative solutions shown in Table 1 was poured into a syringe. 15 μL each of the PEG derivative solution was spotted on 6 points of chip F at the same positions as those in (5-2) above at intervals of 18 mm. The diameter of a droplet was approximately 3.5 mm. After such spotting, chip F was placed in a wet box, and the wet box was then hermetically sealed. It was left at rest at 25° C. for 16 hours.

(5-5) Washing

The sample removed from the wet box was washed with pure water.

As shown in Table 1, the operations described in (5-2) to (5-5) above were repeatedly performed on the same position 1 to 3 times, so as to prepare a surface that did not retain a physiologically active substance. The obtained sample was called chip G.

(6) Formation of Surface that Retains Physiologically Active Substance

A surface portion that retains a physiologically active substance was formed on the surface of chip G by the following method. Specifically, using the COOH group of 5-aminovaleric acid existing on the surface of chip G, α-amino-ω-carboxyl-polyethylene glycol (average molecular weight:3,400) was allowed to covalently bind to a specific area of chip G.

(6-1) Preparation of Reaction Solutions 0.1 M Sulfo-NHS solution:2.04 g of NHS was dissolved in ultrapure water, so as to prepare 100 mL of the solution.

0.4 M EDC solution:7.7 g of EDC was dissolved in ultrapure water, so as to prepare 100 mL of the solution.

10% α-amino-ω-carboxyl-polyethylene glycol solution:10 g of α-amino-ω-carboxyl-polyethylene glycol (average molecular weight:3,400) was dissolved in 80 mL of ultrapure water, and the pH of the solution was then adjusted to pH 8.5 by addition of 1 N NaOH. Ultrapure water was further added thereto to a final volume of 100 mL.

(6-2) Activation

Chip G was drained using an air gun, and it was then immobilized on the seating of a dispenser manufactured by Musashi Engineering, Inc. Subsequently, a mixed solution of 2 mL of the 0.1M Sulfo-NHS solution and 2 mL of the 0.4M EDC solution was poured into a syringe. The central position was set at 4.5 mm deviated from the spotting position in (5-4) above, and 15 μL each of the above Sulfo-NHS/EDC mixed solution was spotted on 6 points of chip G at intervals of 18 mm. The diameter of a droplet was approximately 3.5 mm. After such spotting, chip G was placed in a wet box, and the wet box was then hermetically sealed. It was left at rest at 25° C. for 60 minutes.

(6-3) Washing

The sample removed from the wet box was washed with pure water. The obtained sample was called chip H.

(6-4) Binding of α-amino-ω-carboxyl-polyethylene glycol

Chip H was drained using an air gun, and it was then immobilized on the seating of a dispenser manufactured by Musashi Engineering, Inc. Subsequently, a 10% α-amino-ω-carboxyl-polyethylene glycol solution was poured into a syringe. 15 μL each of the α-amino-ω-carboxyl-polyethylene glycol solution was spotted on 6 points of chip H at the same positions as in (6-2) above at intervals of 18 mm. The diameter of a droplet was approximately 3.5 mm. After such spotting, chip H was placed in a wet box, and the wet box was then hermetically sealed. It was left at rest at 25° C. for 16 hours.

(6-5) Washing

The sample removed from the wet box was washed with pure water. The obtained sample was called chip I.

(6-6) Conservation

Chip I was drained using an air gun, and it was then conserved.

Subsequently, the non-specific adsorption amounts of a protein and a low molecular weight compound on the produced surface that does not retain a physiologically active substance were evaluated.

(1) Measurement of Non-Specific Adsorption Amount of Protein 0.5 mg of fibrinogen (manufactured by MP Biomedicals) was dissolved in 0.5 ml of an HBS-EP buffer (manufactured by Biacore). The composition of the HBS-EP buffer consists of 0.01 mol/l HEPES (N-2-hydroxyethylpiperazine-N'-2-ethanesulfonic acid (pH 7.4)), 0.15 mol/l NaCl, 0.003 mol/l EDTA, and 0.005% by mass of Surfactant P20. The HBS-EP buffer was flown as a running buffer over an SPR device, and a reference point was determined. Thereafter, the prepared fibrinogen solution was flown over it for 3 minutes, and the HBS-EP buffer was then flown over it for 3 minutes. An increase in the SPR signal from the reference point was defined as a non-specific adsorption amount. The measurement results are shown in Table 1.

(2) Measurement of Non-Specific Adsorption Amount of Low Molecular Weight Compound Compound A was dissolved in an HBS-N buffer (manufactured by Biacore)/5% DMSO solution, resulting in a concentration of 0.1 mM. The composition of the HBS-N buffer consists of 0.01 mol/l HEPES (N-2-hydroxyethylpiperazine-N'-2-ethanesulfonic acid (pH 7.4)) and 0.15 mol/l NaCl. The HBS-N buffer/5% DMSO solution was flown as a running buffer over an SPR device, and a reference point was determined. Thereafter, the prepared compound A solution was flown over it for 3 minutes, and the HBS-N buffer/5% DMSO solution was then flown over it for 3 minutes. An increase in the SPR signal from the reference point was defined as a non-specific adsorption amount. The measurement results are shown in Table 1.

TABLE 1

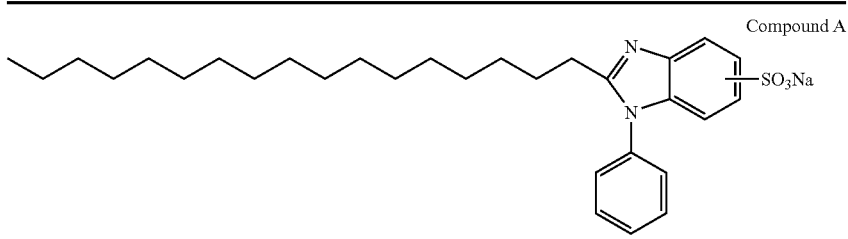

Compound A

| Experiment No. | Binding reaction of hydrophilic compound | | | Amount of non-specific adsorption (RU) | | Remarks |
|---|---|---|---|---|---|---|
| | 1$^{st}$ reaction | 2$^{nd}$ reaction | 3$^{rd}$ reaction | Fibrinogen | Compound A | |
| 1 | None | None | None | 1450 | 1230 | Comparative example |
| 2 | PEG derivative (1) | None | None | 270 | 1120 | Comparative example |
| 3 | PEG derivative (1) | PEG derivative (1) | PEG derivative (1) | 110 | 1060 | Comparative example |
| 4 | PEG derivative (2) | Non | Non | 420 | 1050 | Comparative example |
| 5 | PEG derivative (2) | PEG derivative (2) | PEG derivative (2) | 180 | 1010 | Comparative example |
| 6 | PEG derivative (3) | Non | Non | 780 | 520 | Comparative example |
| 7 | PEG derivative (3) | PEG derivative (3) | PEG derivative (3) | 650 | 350 | Comparative example |

TABLE 1-continued

Compound A: a benzimidazole derivative with a long alkyl chain, N-phenyl substituent, and SO₃Na group.

| Experiment No. | Binding reaction of hydrophilic compound | | | Amount of non-specific adsorption (RU) | | Remarks |
|---|---|---|---|---|---|---|
| | 1st reaction | 2nd reaction | 3rd reaction | Fibrinogen | Compound A | |
| 8 | PEG derivative (1) | PEG derivative (3) | Non | 60 | 90 | The present invention |
| 9 | PEG derivative (2) | PEG derivative (3) | Non | 70 | 80 | The present invention |
| 10 | PEG derivative (1) | PEG derivative (2) | PEG derivative (3) | 40 | 50 | The present invention |

From the results shown in Table 1, it is found that the amount of non-specific adsorption is suppressed in the chip of the present invention.

Effects of the Invention

In the biosensor of the present invention, two or more types of hydrophilic compounds with different molecular weights are allowed to bind to the surface that does not retain a physiologically active substance, so as to prevent non-specific adsorption of proteins, low molecular compounds or the like. When only hydrophilic compound with small molecular weight is used, the effect of preventing the non-specific adsorption of proteins is small. On the other hand, when only hydrophilic compound with large molecular weight is used, the effect of preventing the non-specific adsorption of low molecular compounds cannot be prevented. In the present invention, however, the non-specific adsorption of proteins and that of low molecular compounds can be simultaneously prevented.

The invention claimed is:

1. A biosensor which comprises a substrate having at least two types of surfaces on a single plane, wherein at least one type of said surfaces retains a physiologically active substance and at least one other type of said surfaces does not retain a physiologically active substance, and wherein at least two types of hydrophilic compounds with different molecular weights are covalently bound to a self-assembling film or a hydrophobic polymer layer on said surface that does not retain the physiologically active substance, wherein said hydrophilic compounds are represented by $NH_2-(CH_2CH_2O)_n-CH_2CH_2OH$,
wherein the average molecular weight of a hydrophilic compound with the smallest molecular weight is between 100 and 1,000, and
wherein the average molecular weight of a hydrophilic compound with the largest molecular weight is between 1,000 and 1,000,000.

2. The biosensor according to claim 1, which is obtained by allowing at least two types of hydrophilic compounds with different molecular weights to bind to the surface that does not retain the physiologically active substance in decreasing order of the molecular weight of each type of compound.

3. The biosensor according to claim 1, wherein the difference between the average molecular weight of the at least two types of hydrophilic compounds is at least 500.

4. The biosensor according to claim 1 wherein the substrate is composed of a metal surface or metal film.

5. The biosensor according to claim 4, wherein the metal surface or metal film consists of a free electron metal selected from the group consisting of gold, silver, copper, platinum, and aluminum.

6. The biosensor according to claim 1, which is used in non-electrochemical detection.

7. The biosensor according to claim 1, which is used in surface plasmon resonance analysis.

8. A method for immobilizing a physiologically active substance on the surface of a biosensor, which comprises a step of allowing the biosensor according to claim 1 to come into contact with the physiologically active substance, so as to prepare a surface to which said physiologically active substance has been bound, and a surface to which said physiologically active substance has not been bound, on said biosensor surface.

9. A method for detecting or measuring a test substance interacting with a physiologically active substance, which comprises a step of allowing the test substance to come into contact with the biosensor which was produced by the method of claim 8.

10. The method of claim 9, wherein the test substance interacting with the physiologically active substance is detected or measured by a non-electrochemical method.

11. The method of claim 9, wherein the test substance interacting with the physiologically active substance is detected or measured by surface plasmon resonance analysis.

* * * * *